Figure 1:
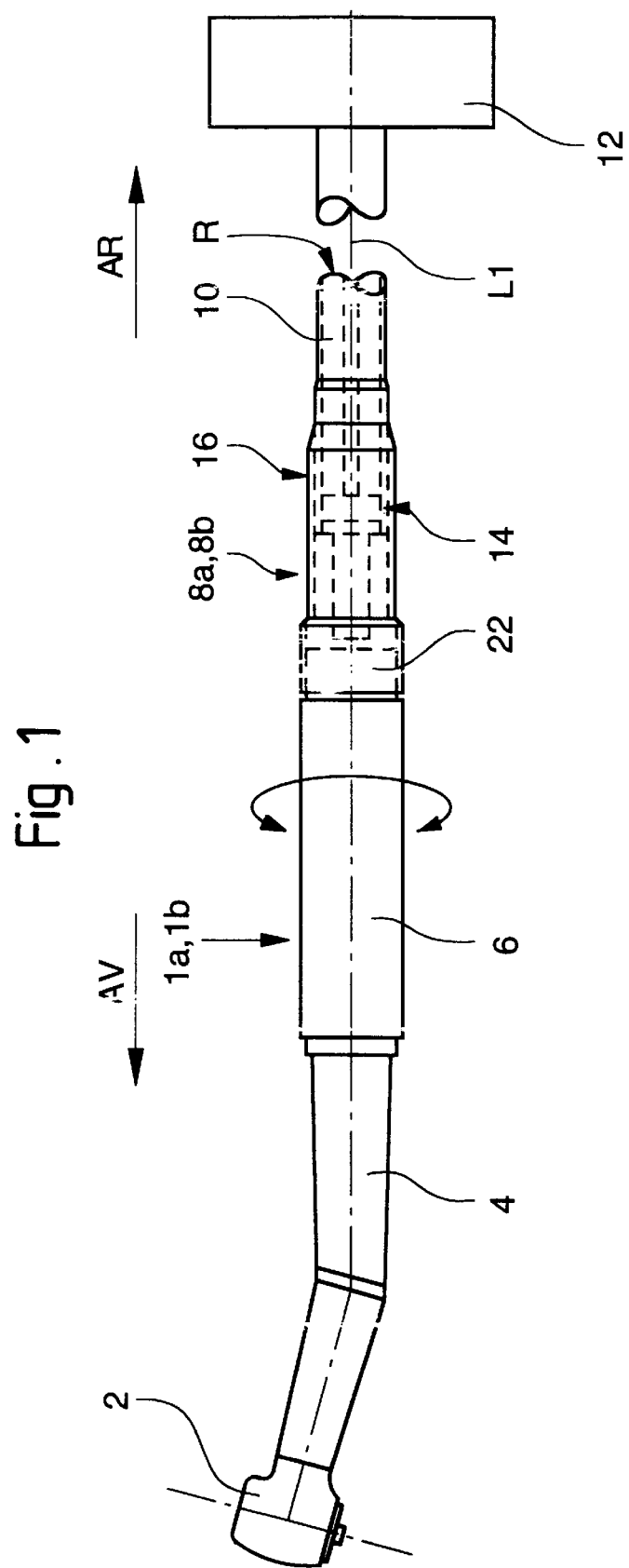

United States Patent
Mosimann

[11] Patent Number: 6,033,220
[45] Date of Patent: Mar. 7, 2000

[54] MULTI-PURPOSE REVOLVING CONNECTING ASSEMBLY

[75] Inventor: Vincent Mosimann, La Neuveville, Switzerland

[73] Assignee: Bien-Air S.A., Bienne, Switzerland

[21] Appl. No.: 09/319,432

[22] PCT Filed: Dec. 22, 1997

[86] PCT No.: PCT/EP97/07243

§ 371 Date: Jun. 7, 1999

§ 102(e) Date: Jun. 7, 1999

[87] PCT Pub. No.: WO98/29052

PCT Pub. Date: Jul. 9, 1998

[30] Foreign Application Priority Data

Dec. 27, 1996 [FR] France ................................. 96 16129

[51] Int. Cl.$^7$ ................................................. A61C 9/00
[52] U.S. Cl. ................................................. 433/126
[58] Field of Search .................... 433/126, 115, 433/29

[56] References Cited

U.S. PATENT DOCUMENTS

| | | | |
|---|---|---|---|
| 5,057,015 | 10/1991 | Fleer | 433/126 |
| 5,476,379 | 12/1995 | Disel | 433/126 X |
| 5,511,977 | 4/1996 | Futch, Jr. | 433/126 |
| 5,733,117 | 3/1998 | Coss et al. | 433/126 X |
| 5,868,571 | 2/1999 | Nakanishi | 433/126 X |

FOREIGN PATENT DOCUMENTS

| | | |
|---|---|---|
| 0 369 043 | 5/1990 | European Pat. Off. . |
| 0 393 364 | 10/1990 | European Pat. Off. . |
| 2 733 680 | 11/1996 | France . |

*Primary Examiner*—Nicholas D. Lucchesi
*Attorney, Agent, or Firm*—Griffin, Butler, Whisenhunt & Szipl, LLP

[57] ABSTRACT

The invention concerns a multi-purpose revolving connecting assembly intended to connect dental instruments (1*a*, 1*b*) having rear portions (22) of different geometrical configurations to a supply source (S).

This connecting assembly is characterized in that it includes a nut (16) formed, at the front, of a removable sleeve (50*a*, 50*b*) and, at the rear, of a bush (52) which can be connected to the sleeve (50*a*, 50*b*) by a screw-nut system, the sleeve (50*a*, 50*b*) being provided to be fixed onto the dental instrument (1*a*, 1*b*), while the socket (52) has a support surface (58*b*) intended to abut against the ring (4) axially holding a mobile coupling piece (28*a*, 28*b*) on a fixed coupling piece (26).

8 Claims, 4 Drawing Sheets

MULTI-PURPOSE REVOLVING CONNECTING ASSEMBLY

The present invention concerns a multi-purpose revolving connecting assembly capable of connecting different types of dental instruments to a power supply.

More particularly, this invention concerns a revolving connecting assembly capable of being connected to dental instruments whose rear portions, which are intended to assure the connection thereof to the connecting assembly, have different geometrical configurations to each other.

Conventional dental equipment which is used by dental practitioners for dental treatments, is generally formed of a power supply which is designated, in the profession, by the term <<unit>> and which is capable of providing the agents and power necessary for implementing said treatments.

This equipment generally includes several supply hoses, one end of which is connected to the unit, while the other end is intended to be coupled, via a specific coupling socket, to the rear of one or more dental instruments which are available on a display cabinet.

In order to be mechanically fixed onto an instrument, each coupling socket is generally fitted with a rotating nut which is arranged to be screwed onto the rear of such instrument, the latter including a threading provided for such purpose.

This assembly, formed of the hose, socket and rotating nut, is designated, in dental circles, by the term <<connecting assembly>>.

Thanks to this socket and the nut, according to the operations which the has to perform, the dental practitioner can fit the necessary instruments to the respective connecting assemblies of his equipment as a function of their compatibility.

For reasons of simplification, rationalization and economy, it is sought to improve this compatibility and to allow the connection of the largest number of instruments or even all the instruments to a same connecting assembly, and to fit the equipment with several connecting assemblies of the same type, or even a single connecting assembly capable of assuring the connection of all the instruments to the unit.

The instruments which exist on the market and with which dental practitioners are already provided, have rear portions of different geometrical configurations, i.e. of different shape/and or dimensions, which stands in the way of such compatibility.

Thus, an object of the present invention is to provide a revolving connecting assembly solving this problem which can, via a simple, inexpensive solution, allow connection to different types of dental instruments having rear portions of different geometries.

The invention therefore concerns a multi-purpose revolving connecting assembly including:

a hose including coupling means, such as at least one electric power cable and/or at least one fluid conveying conduit, these coupling means being intended to be connected to the power supply, a connector provided for assuring the coupling, at the front of the connecting assembly, between a dental instrument and the coupling means, this connector being formed of a first fixed coupling piece attached to the coupling means and a second mobile and removable connection, which can be connected to the first coupling piece and which is provided to be connected to the dental instrument, the second coupling piece being able to be rotatably mounted and held axially on the first coupling piece via a rotating stopping ring, blocked axially on the first coupling piece and able to be screwed onto the second coupling piece, and a nut able to be fixed to the rear portion of the instrument and, including a support face intended to abut against a corresponding shoulder of the connecting assembly in order to push and install the connector onto the rear portion of the dental instrument, when the nut is screwed in, this connecting assembly being characterized in that the nut is formed, at the front, of a removable sleeve and, at the rear, of a bush which can be connected to the sleeve by a screw-nut system, the sleeve being provided to be fixed to the dental instrument, while the bush has a support surface intended to abut against the ring.

Figure 2:
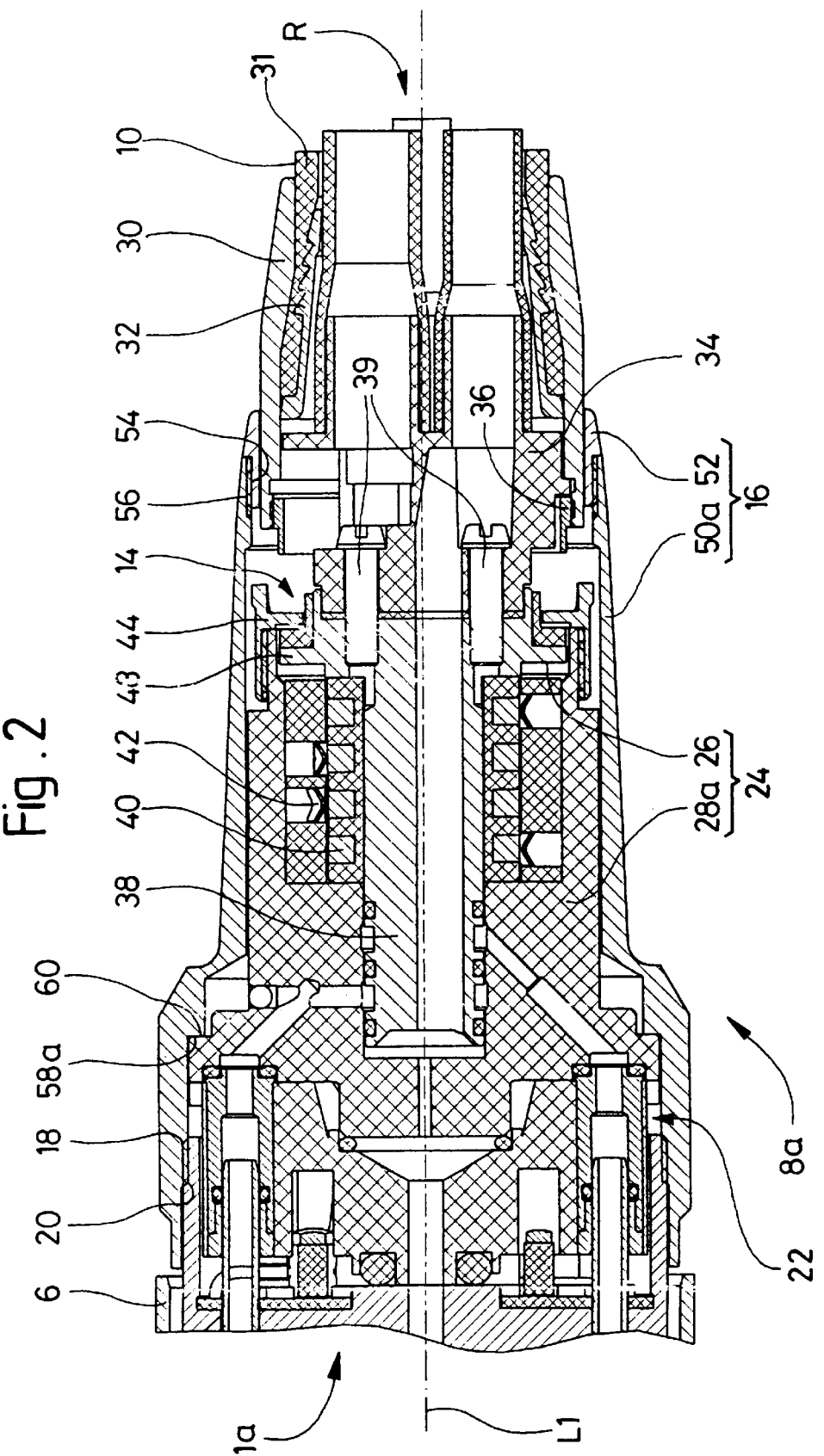
Figures 3, 3A:
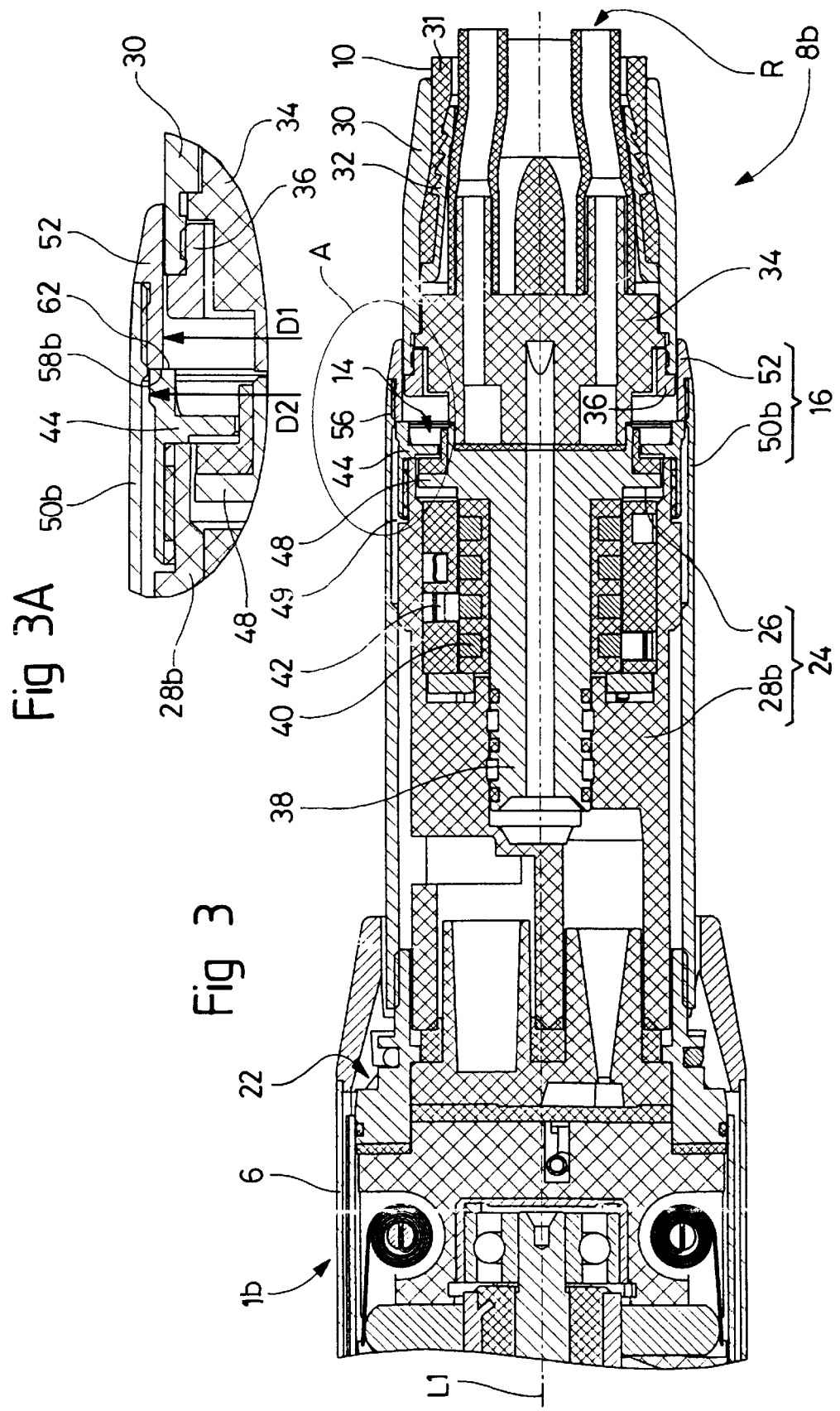
Figure 4:
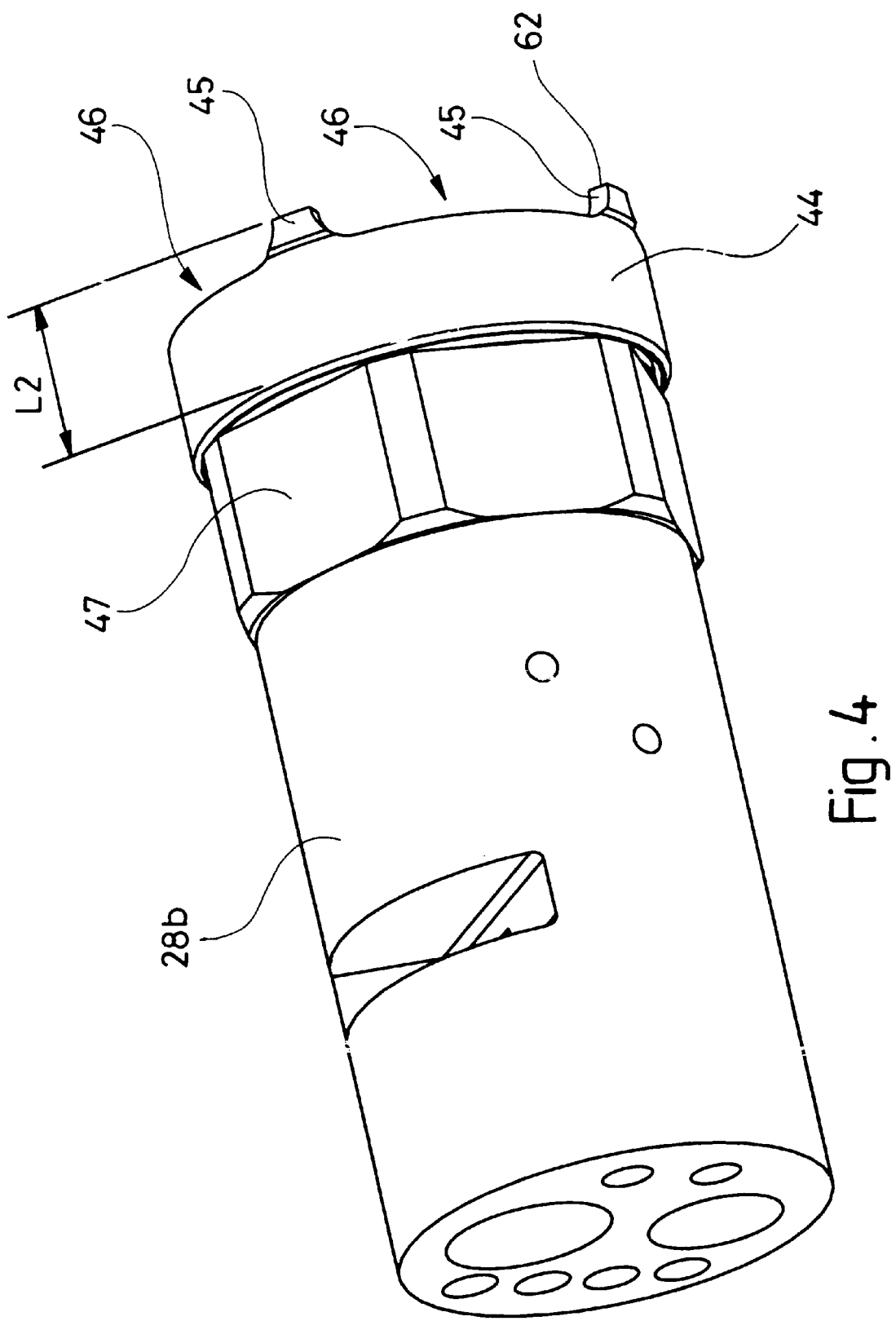

Other features and advantages of the invention will appear upon reading the following detailed description, given with reference to the annexed drawings which are given solely by way of example, and in which:

FIG. 1 is a schematic side view of a dental apparatus including an instrument connected to a connecting assembly according to the invention, FIG. 2 is a longitudinal cross-section of a connecting assembly connected to the rear of a dental instrument of a first type, the rear of which has a first configuration, FIG. 3 is a similar cross-section to that of FIG. 2, but showing the connecting assembly of FIG. 2 connected to the rear of a dental instrument of a second type and the rear of which has a second configuration, FIG. 3A is an enlargement of zone A of FIG. 3, and FIG. 4 is a perspective view of a stopping ring and a mobile coupling piece fitted to the connecting assembly of FIG. 3.

With reference now to FIG. 1, a dental apparatus which includes a conventional instrument 1a, 1b, formed in this example of a contra-angle, which is provided, at the front end thereof, with a head 2, arranged for accommodating a tool, not shown, will be described hereinafter.

In the present Application, <<the front>> will be defined as the region of the apparatus extending in the direction of head 2 (arrow AV) and <<the rear>> will be defined as the region of the apparatus extending in the opposite direction (arrow AR), i.e. in the direction of a unit S to which instrument 1a, 1b is connected.

At the rear of the body of instrument 1a, 1b, and more particularly at the rear of the sleeve 4 thereof, there is connected a motor 6 which can be disconnected from sleeve 4 simply by traction.

Motor 6 is further connected, at the rear, to a connecting assembly 8a, 8b which includes a supply hose 10 connected to unit S which forms an electric power and fluid supply source.

This connecting assembly 8a, 8b further includes a socket 14 inside which are arranged several unreferenced connection elements, including several fluid conveying channels and several electric contacts and electric feed wires.

Supply hose 10 also includes several fluid conveying conduits and several electric feed wires (also unreferenced) forming coupling means R which are connected to unit S and which are respectively connected to the channels and wires of coupling socket 14.

It will be specified that these fluid conveying channels and conduits allow air to be supplied to the apparatus, which is used to power a motor if instrument 1a, 1b is a turbine or compressed air motor, or possibly as cooling air, if instrument 1a, 1b is a contra-angle coupled to an electric motor 6, as in the example shown.

These channels and conduits can also assure the evacuation of outgoing air to the rear of the apparatus, in the direction of unit S, and/or can be used to bring the air and water necessary for the cooling spray, which is intended to be sprayed over the working area of the tool which is carried and driven by head 2.

The electric wires and contacts of all these components allow power to be supplied to electric motor 6 and/or a light, which can be for example housed within motor 6 and which can be associated with optical fibers guiding the light to head 2, in the direction of the working area.

It will further be specified that hose 10 and socket 14 can include other wires, channels and/or conduits, not shown, having functions which it is not necessary to describe here.

Although the description here is of a connecting assembly and an instrument including several coupling means formed of channels, conduits and connection wires, it will be understood that the invention also applies to an arrangement including only one conduit and/or one fluid conveying channel, and/or one electric feed wire.

The rear portion 22 of instrument 1*a*, 1*b* which is shown partially in the drawings, is described, in this particular example, as belonging to a component of a motor. This motor forms part, in the wide sense, of a range of several types of apparatus or components intended for dental treatment and having different functions, these apparatus, including the motor presently described, being all classified here as <<dental instruments>>, whether they are used directly or indirectly during the treatment.

Connecting assembly 8*a*, 8*b* which forms the subject of the present invention and which will be described hereinafter in more detail, is capable of being connected advantageously to different types of dental instruments the rear portions of which have different geometrical configurations.

These instruments which can be a motor as described in this example or in particular a turbine, a turbine coupling, or a contra-angle with a motor are conventional and known to those skilled in the art and will consequently not be described here in detail.

Connecting assembly 8*a*, 8*b* includes a rotating fixing nut 16 in which is arranged, at the front end thereof, an inner threading 18 (FIG. 2) which is arranged to be screwed onto an outer threading 20, provided on rear portion 22 of instrument 1*a*, 1*b*. Although the arrangements of the embodiment examples of FIGS. 1 to 3 have been described and shown with 35 a mechanical coupling, between rotating nut 16 and the rear of instrument 1*a*, 1*b*, of the screw-nut type (formed by threadings 18 and 20), it will be specified that the invention is not limited to this type of coupling assembly.

It will be noted here that instrument 1*a* which is shown in FIG. 2 and which will be described hereinafter is an instrument of a first type, in particular an electric motor, having a first specific rear configuration.

In order to assure the coupling between unit S and instrument 1a formed by motor 6, socket 14 includes a connector 24 which is formed of two coupling pieces which are respectively fixed 26 and mobile 28*a*, these two coupling pieces being provided to assure the interface and functional link for conveying electric power and fluids between coupling means R of hose 10 and rear 22 of the motor.

In this example, connecting assembly 8*a* includes a hollow body or sleeve 30 in which a sheath 31 made of flexible material is firmly secured, via a gripping sleeve 32. Fixed coupling piece 26 of connector 24 is also engaged and firmly secured in body 30, via an insert 34, secured to body 30 by a screwed-in ring 36.

Fixed coupling piece 26 includes a hollowed longitudinal shaft 38 which is fixed to insert 34 by conventional screws 39. This shaft 38 carries radial electric contacts 40 (only one of which is referenced) which are fixed to shaft 38 and which cooperate with corresponding electric contacts 42, carried by mobile coupling piece 28*a*.

It is to be noted that due to the fixing thereof to hose 10, via insert 34, screws 39, and ring 36, fixed coupling piece 26 is intended to remain immobile on connecting assembly 8*a*, except during maintenance operations.

As will be understood from the following description, this fixed portion 26 of connector 24 is intended to remain permanently on connecting assembly 8*a*.

It will also be noted that mobile coupling piece 28*a* of connector 24 and shaft 38 of fixed coupling piece 26 include fluid conveying channels, and various unreferenced bores, grooves and orifices, which allow fluid or fluids to be conveyed from coupling means R, to instrument 1*a*. These elements also include various conventional sealing means, such as O-ring type sealing rings which will not be described in more detail.

Rear 22 of the instrument also includes a set of coupling means also formed of various fluid conveying channels, bores, grooves and orifices, but also electric contacts and wires which will not be described either, since the design thereof is conventional and within the grasp of those skilled in the art.

As will be understood, mobile coupling piece 28*a* can rotate on fixed coupling piece 26, with contacts and a friction fitting which assure a good connection between these two coupling pieces.

Mobile coupling piece 28*a* can however, in use, be immobilized axially on shaft 38 and with respect to fixed coupling piece 26, via a rotating stopping ring 44 the front of which is screwed onto the rear of mobile coupling piece 28*a*.

For this purpose, shaft 38 of fixed coupling piece 26 includes a collar 48 which, in this example, is associated with a bearing (unreferenced) with a low friction coefficient.

Collar 48 is confined axially between ring 44 and mobile coupling piece 28*a*.

It will be noted in FIGS. 2 and 3 that this arrangement has operating plays such as that stopping ring 44 can be screwed and gripped against mobile coupling piece 28*a*, without the ring 44-connection 28*a* assembly being wedged onto collar 48, and thus onto fixed coupling piece 26. Thus, ring 44, mobile coupling piece 28*a*, rear 22 of instrument 1*a* and nut 16 can rotate together, around fixed coupling piece 26 and with respect to longitudinal axis of connecting assembly 8a and hose 10, to allow the instrument to rotate in this region of the apparatus, in order to offer the dental practitioner greater freedom of movement in his manipulations during treatment.

Nut 16 of connecting assembly 8*a* is advantageously formed, at the front, of a removable sleeve 50*a* and, at the rear, of a bush 52 which can be connected to sleeve 50*a* by a screw-nut system, formed of a first threading 54 arranged at the front of bush 52 and a second threading 56 which is intended to be screwed onto the first and which is arranged at the rear of sleeve 50*a*. On the other side sleeve 50*a* is arranged to be fixed onto the rear of dental instrument 1*a*, in particular via threadings 18 and 20, which allows connecting assembly 8*a* and dental instrument 1a to be firmly secured mechanically.

In this coupling between this first type of instrument 1*a*and this first type of sleeve 50*a*, the contact under pressure between rear 22 of instrument la and mobile coupling piece 28*a* is achieved via a first support surface 58*a* arranged, in this example, in the bottom of a housing of sleeve 50*a*, close to threading 18. This support surface 58*a* has the shape of an annular shoulder which cooperates via axial pressure on shoulder 60, arranged in this example on mobile coupling piece 28a, and against which support surface 58a of sleeve 50 abuts when nut 16 is screwed onto rear portion 22 of motor 1a. One thereby assures that there is contact and sealed communication between the coupling means of connecting assembly 8a and the coupling means of instrument 1a.

With reference now to FIG. 3 which shows a connecting assembly 8a according to the invention, coupled to an instrument 1b of a second type, formed in this example by an electric motor having a rear portion with a second specific configuration.

For the sake of simplification, in FIG. 3 the parts similar to those previously described are designated with the same references as those used hereinbefore.

As is seen in FIG. 3, removable sleeve 50b of nut 16 is different to sleeve 50a shown in FIG. 2. More particularly, the length of these removable sleeves 50a and 50b and the geometry of the front portion thereof are adapted to the type of instrument 1a, 1b to which connecting assembly 8a, 8b has to be connected.

Moreover, connecting assembly 8b of FIG. 3 is provided with a different mobile coupling piece 28b to mobile coupling piece 28a which is fitted to connecting assembly 8a, in order to assure that this connecting assembly 8b is adapted to the rear of instrument 1b.

It will be noted however that between these two configurations, the same connecting assembly base has been preserved, since hose 10, fixed coupling piece 26 with its shaft 38 and electric contacts 40 and stopping ring 44 are the same for both connecting assemblies.

Different constructive details can be seen in FIGS. 2 and 3, in particular as regards hose 10, insert 34 and shaft 38 since, in the two FIGS. 2 and 3, these elements have been shown along different cross-section planes.

It is clear that the connection of this same connecting assembly base to instruments of different geometry is achieved by changing mobile and removable coupling pieces 28a and 28b and by changing mobile and removable sleeves 50a and 50b, the change of mobile and removable coupling pieces 28a and 28b being achieved by unscrewing and screwing stopping ring 44.

By way of indication, the total length L2 of stopping ring 44 (FIG. 4) is around 5 mm. This ring 44 includes at the periphery thereof, and in particular at the rear, fingers 45 (here four at 90°) which project from the rear of ring 44, in a longitudinal direction and which also extend in a radial direction. These fingers 45 constitute amongst other things means for gripping ring 44 which allow it to be manipulated in rotation.

Thus, stopping ring 44 has a length and a shape such that it can be easily held in the hand. In this example, ring 44 is thus provided to be able to be actuated manually in order in particular to allow a technician to screw it and unscrew it to change mobile and removable coupling piece 28a with another type of connection 28b. Of course, ring 44 could be given a different shape to allow it to be actuated for example by a specific tool.

It is also to be noted that the range of mobile coupling pieces and the range of sleeves is not limited to that described, but can be extended to other types of coupling pieces and sleeves, as a function of the geometry of the instruments which one wishes to fit to the connecting assembly.

In the two examples described, it will be noted that sleeve 50a, 50b has a considerably longer length than that of bush 52, this sleeve 50a, 50b covering removable coupling piece 28a, 28b of connector 24, and stopping ring 44 and extending behind ring 44 to be secured to bush 52. By way of indication, bush 52 has a total length of around 4.2 mm, while sleeves 50a and 50b have total respective lengths of around 35 and 32.2 mm.

Thus, when the technician detaches removable sleeve 50a, 50b from the connecting assembly by unscrewing it, he has direct access to ring 44 without needing to push bush 52 rearwards. Indeed, bush 52 extends essentially behind stopping ring 44, towards the rear of the apparatus, in the direction of hose 10, and only covers hollow body 30. Consequently, in the absence of removable sleeve 50a, 50b, the practitioner may, if he so wishes, grasp both ring 44 and bush 52 which can rotate together. It will further be noted here that ring 44 and bush 52 both remain fixed to the connecting assembly and that they cannot be detached therefrom, at least without disconnecting hose 10 and coupling means R thereof from unit S.

It is to be noted thus that in this arrangement, all the mobile parts of the connecting assembly are removable and may be interchanged, with the exception of stopping ring 44 and bush 52 which remain fixed to the connecting assembly.

Indeed, as is seen in FIGS. 3 and 3A, the inner diameter D1 of socket 52 is, particularly at the front of said bush 52, less than the outer rear diameter of D2 of stopping ring 44, so that stopping ring 44 can act as a stop as regards bush 52 and it can block the axial movement of this bush 52 forwards. Bush 52 can therefore not be lost, if hose 10 is not disconnected from unit S.

Furthermore, sleeve 50b and mobile coupling piece 28b do not, in this arrangement, include axial support surfaces, bush 52 fulfills this axial support function, in place of sleeve 50a (FIG. 2), since it includes at the front thereof a frontal support surface 58b which abuts, at the rear of ring 44, against a support surface 62 formed by the free end of fingers 45.

Thus, when sleeve 50b is screwed onto rear 22 of instrument 1b via threadings 18 and 20, nut 16 pulls the rear of instrument 1b. By resting against ring 44, bush 52 allows mobile coupling piece 28b to be blocked against the rear of instrument 1b, in order to assure the connection between the connecting assembly and instrument 1b.

It will further be noted that frontal support surface 58b of bush 52 constitutes its frontmost edge, so that bush 52 does not extend beyond rear support surface 62 of ring 44, and cannot overlap said ring. It is also to be noted that the screw-nut coupling between bush 52 and sleeve 50a, 50b, comprised of threadings 54 and 56, is formed in this arrangement behind ring 44 and in particular behind support surface 62 thereof.

With reference to FIG. 4, it is seen that fingers 45 of ring 44 delimit between them semi-oblong scallopings 46 opening out radially and allowing communication channels to be arranged between the rear of ring 44 and the front of bush 52, such channels allowing the outlet fluid to flow from the rear of instrument 1b to hose 10. In fact, as seen in FIG. 2, insert 34 is scalloped on the side while the periphery of mobile coupling piece 28b (FIG. 4) includes cavities 47 allowing said fluid to flow between sleeve 50b and said coupling piece 28b. Further, and as is seen in FIG. 3, the rear of sleeve 50b includes, before threading 56, an inner annular chamber 49 which also allows the outlet fluid to flow between ring 44 and sleeve 50b.

It is clear from the foregoing description that a simple connecting assembly has been provided which can be adapted to numerous rear configurations of different dental instruments having different geometries, and this is achieved by the abililty of several and in particular two removable parts, which are easy to dismount, to be interchanged.

I claim:

1. A multi-purpose revolving connecting assembly connecting dental instruments having rear portions of different geometric configurations to a supply source, said connecting assembly including:

a hose including coupling means, said coupling means comprising at least one electric power cable and/or at least one fluid conveying conduit, said coupling means being arranged to be connected to said supply source, a connector provided for assuring the coupling, at the front of the connecting assembly, between a dental instrument and said coupling means, said connector being formed of a first fixed coupling piece attached to the coupling means and a second mobile and removable coupling piece, which can be connected to the first coupling piece and which is arranged to be connected to the dental instrument, the second coupling piece being able to be rotatably mounted and held axially on the first coupling piece via a rotating stopping ring, said stopping ring being blocked axially on the first coupling piece and able to be screwed onto the second coupling piece, and a nut able to be fixed to the rear portion of the instrument and including a support face arranged to abut against a corresponding shoulder of said connecting assembly in order to push and install the connector onto the rear portion of the dental instrument, when the nut is screwed in, wherein said nut is formed, at the front, of a removable sleeve and at the rear, of a bush which can be connected to the sleeve by a screw-nut system, said sleeve being arranged to be fixed to the dental instrument, while said bush has a support surface arranged to abut against said stopping ring.

2. A connecting assembly according to claim 1, wherein said sleeve is substantially longer than said bush.

3. A connecting assembly according to claim 1, wherein said sleeve covers both said mobile coupling piece of the connector, and said stopping ring.

4. A connecting assembly according to claim 1, wherein said sleeve extends essentially behind said ring, in the direction of the hose.

5. A connecting assembly according to claim 1, wherein said screw-nut system connecting said bush to said sleeve extends essentially behind said stopping ring.

6. A connecting assembly according to claim 1, wherein said stopping ring is provided to be actuated by a manual operation, in order to allow a technician to screw it in and unscrew it to change said removable coupling piece for another type of removable coupling piece.

7. A connecting assembly according to claim 1, wherein said stopping ring and said bush are arranged on the connecting assembly to remain fixed thereon.

8. A connecting assembly according to claim 1, wherein said stopping ring has scallopings allowing the passage of an outlet fluid between said stopping ring and said bush.

* * * * *